United States Patent [19]

McCann et al.

[11] Patent Number: 4,488,552
[45] Date of Patent: Dec. 18, 1984

[54] METHOD OF APPLYING THERAPEUTIC HEAT

[75] Inventors: Michael G. McCann; Betty R. McCann, both of Jacksonville, Fla.

[73] Assignee: Micropak Manufacturing, Inc., Orange Park, Fla.

[21] Appl. No.: 372,704

[22] Filed: Apr. 28, 1982

[51] Int. Cl.³ .............................................. A61F 7/00
[52] U.S. Cl. ..................................... 128/402; 128/403
[58] Field of Search ................................. 128/399–400, 128/402–403, 379, 804; 219/10.55 R

[56] References Cited

U.S. PATENT DOCUMENTS

| | | | |
|---|---|---|---|
| 915,452 | 3/1909 | Litts | 150/52 R |
| 1,819,807 | 8/1931 | Baysinger | 44/3 A |
| 1,927,751 | 9/1933 | Mensi | 150/52 R |
| 2,249,936 | 7/1941 | Birtcher | 128/804 |
| 2,288,745 | 7/1942 | Sammis | 62/331 |
| 2,563,933 | 8/1951 | Hipps et al. | 383/86 |
| 2,590,212 | 3/1952 | Samuels | 604/291 |
| 2,814,298 | 11/1957 | Argento | 128/798 |
| 3,244,210 | 4/1966 | Clarizio | 383/35 |
| 3,527,654 | 9/1970 | Jones et al. | 428/81 |
| 3,628,537 | 12/1971 | Berndt et al. | 128/402 |
| 3,815,610 | 6/1974 | Winther | 128/380 |
| 3,861,389 | 1/1975 | Winther | 219/85 R |
| 3,867,939 | 2/1975 | Moore et al. | 128/400 X |
| 3,874,504 | 4/1975 | Verakas | 128/403 X |
| 3,889,684 | 6/1975 | Lebold | 128/402 |
| 3,980,070 | 9/1976 | Krupa | 128/263 |
| 4,056,646 | 11/1977 | Westfall et al. | 428/90 |
| 4,107,509 | 8/1978 | Scher et al. | 219/211 |
| 4,163,896 | 8/1979 | McAvinn et al. | 219/525 |
| 4,204,549 | 5/1980 | Paglione | 128/784 |
| 4,310,738 | 1/1982 | Moretti et al. | 219/10.55 R X |
| 4,326,533 | 4/1982 | Henderson | 128/403 X |

FOREIGN PATENT DOCUMENTS

| | | | |
|---|---|---|---|
| 0762734 | 12/1956 | United Kingdom | 128/399 |
| 1167481 | 10/1969 | United Kingdom | 128/403 |
| 1345261 | 1/1974 | United Kingdom | 128/403 |
| 1383536 | 2/1975 | United Kingdom | 128/403 |

*Primary Examiner*—Lee S. Cohen
*Assistant Examiner*—Angela D. Sykes
*Attorney, Agent, or Firm*—Cushman, Darby & Cushman

[57] ABSTRACT

A method of applying therapeutic heat, and a heat pack for providing therapeutic heat-transfer, are simple, inexpensive to use and practice, and readily re-usable. A piece of polyurethane foam wrapped by an absorbent material such as terry cloth or cotton batting, is saturated with water, placed in an inner nylon bag, and disposed in an envelope made of foam-lined flocked fabric, to form the pack. The pack is placed in a microwave oven to heat the water, and when removed is placed on a body part to be treated. The pack may be reheated and re-used, without opening, repeatedly. The outer covering is longer than the inner core, and can be folded-over to provide several thicknesses of insulation on one face of the pack, while the other face has a single thickness.

8 Claims, 6 Drawing Figures

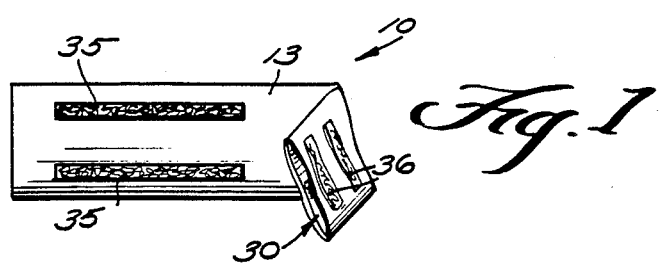
Fig. 1
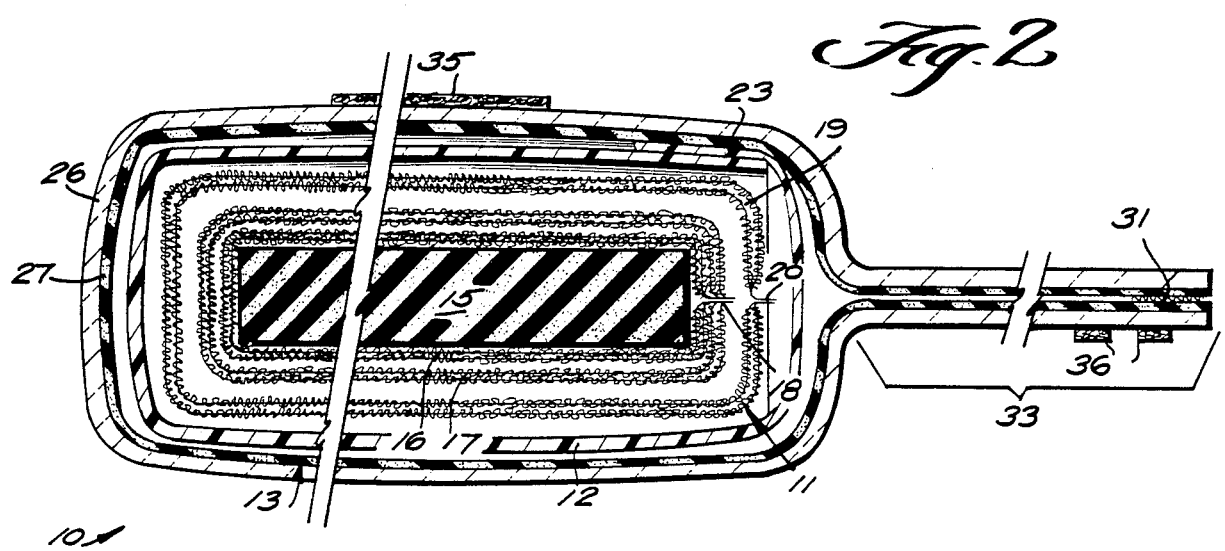
Fig. 2
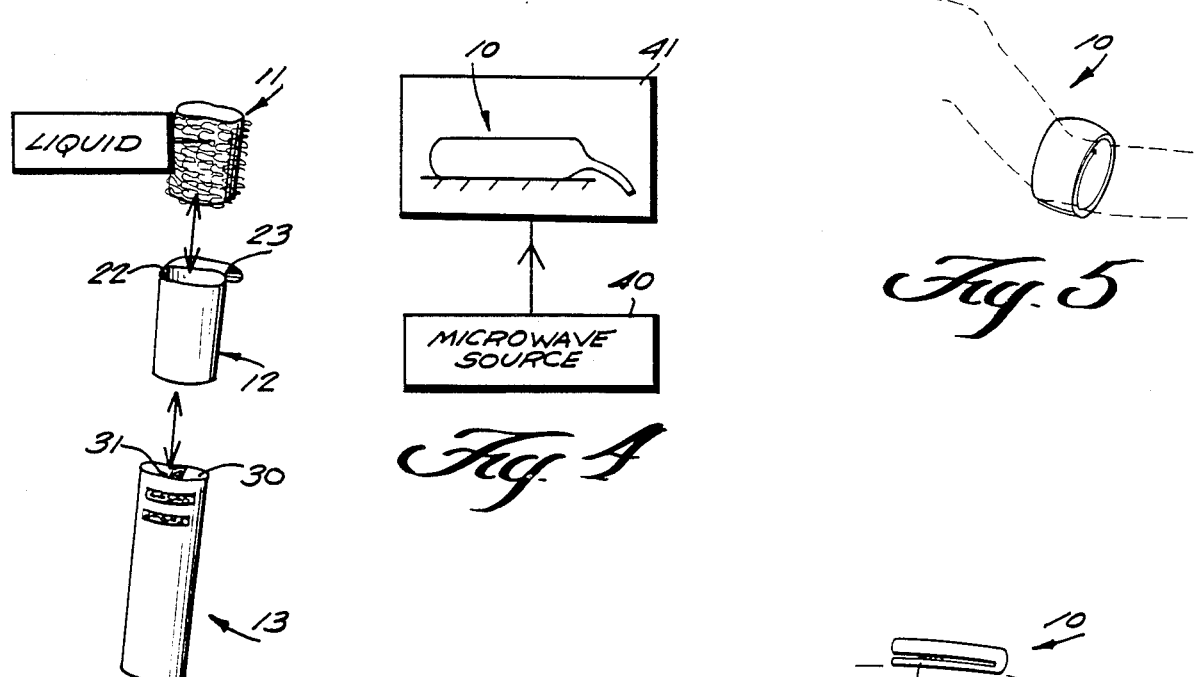
Fig. 3
Fig. 4
Fig. 5
Fig. 6

METHOD OF APPLYING THERAPEUTIC HEAT

BACKGROUND AND SUMMARY OF THE INVENTION

Therapeutic heat-transfer can be very useful in relieving aches, pains, and tension in human and other mammals, enhancing blood circulation or reducing swelling, or the like. The art is replete with procedures and mechanisms which effect therapeutic heat-transfer (either applying heat or cold) to body parts. What such procedures and devices strive to achieve is the application of penetrating heat-transfer in a readily utilizable, and safe manner. The mechanisms for effecting the heat transfer also preferably are simple, inexpensive and readily re-usable.

According to the present invention, a method of applying therapeutic heat to a body part, and a therapeutic heat-transfer pack, are provided which, it is believed, achieve the objectives set forth above. The method and pack according to the present invention overcome many of the disadvantages inherent in conventional devices and procedures. Unlike conventional chemical steam packs, the pack according to the present invention is inexpensive and quickly and readily re-utilizable, no long "soaking" times or reheating cycles being necessary. The method and pack according to the present invention are also less expensive and safer than many conventional electric heating devices for applying moist heat or the like, and are more readily utilizable and retain the desired heat-transfer capabilities for a longer period of time than other conventional hot or cold packs.

Quick, simple, efficient heating, and re-heating, of a heat pack are provided according to the method of the present invention. A heat pack utilized in practicing the present invention includes a liquid-absorbing inner core (such as an absorbent cotton material and polyurethane foam) disposed in a liquid-impervious microwave-transparent inner bag (such as a nylon film bag), and in an outer microwave-transparent covering such as a foam-lined fabric outer covering. Water is applied to the core so that the core is substantially saturated. The core is disposed in the inner bag, and the inner bag is closed, as by folding over the end covering the access opening thereto. The closed inner bag and core are disposed in the outer covering, and then the heat pack is disposed in operative association with a microwave source to heat the liquid associated with the core. After a few minutes of exposure to the microwave source (e.g., about two to seven minutes), the heat pack is removed from association with the microwave source and placed in contact with the body part to be treated. When the pack cools, it may be readily re-utilized merely by re-disposing it in association with the microwave source (there being no necessity to gain access to the interior of the pack) and then reapplying it to the body part.

Also according to the present invention, a therapeutic heat-transfer pack is provided which is capable of applying therapeutic cold as well as therapeutic heat. The pack according to the present invention includes an inner core including a piece of liquid absorbing foam, such as polyurethane foam about half an inch thick, surrounded by absorbent cloth, preferably cotton, (e.g., a plurality of layers of terry cloth) and held in relationship therewith, as by stitching. The pack further comprises an inner bag of thermoplastic material holding the inner core therein, the inner bag preferably being a nylon bag or like microwave-transparent bag that may be re-used indefinitely without sticking together of the bag components. The pack further comprises an outer covering of foam-backed fabric surrounding the inner bag and holding the inner bag and core therein. Preferably the outer covering is formed from self-lining drapery fabric, or a like covering having good insulation qualities, good shape retention, and washability.

According to one embodiment of the heat-transfer pack according to the present invention, the outer covering is substantially longer than the inner core and inner bag so that it is "doubled over" when closed. This—in a simple manner—provides the pack with two surfaces of different heat-transfer ratios. The doubled-over surface may be initially applied against the body when the pack is too "hot" (e.g., just removed from association with a microwave source), or too "cold". After the temperature of the pack equalizes somewhat with the ambient temperature, the single-thickness side of the pack can be applied to the body part, that portion of the pack no longer being to hot or cold.

It is the primary object of the present invention to simply and effectively apply therapeutic heat, or therapeutic heat-transfer, to body parts. This and other objects of the present invention will become clear from an inspection of the detailed description of the invention, and from the appended claims.

BRIEF DESCRIPTION OF THE DRAWINGS

FIG. 1 is a side view of an exemplary assembled heat-transfer pack according to the present invention;

FIG. 2 is a cross-sectional view of the pack of FIG. 1, with individual components thereof magnified for clarity of illustration;

FIGS. 3 through 5 show schematically various steps in the practice of applying therapeutic heat to a body part according to the method of the present invention; and FIG. 6 schematically illustrates an alternative manner of utilizing an exemplary heat-transfer pack according to the present invention for applying therapeutic heat-transfer to a body part.

DETAILED DESCRIPTION OF THE DRAWINGS

An exemplary heat-transfer pack according to the present invention is shown generally by reference numeral 10 in the drawings. The various components of the pack are illustrated most clearly in FIGS. 2 and 3, and include three major components, an inner core 11, and inner bag 12, and an outer covering 13.

The inner core 11 comprises a piece of foam 15 with multiple wrappings of terry cloth or other aborbent cotton materials. The piece of foam 15 may comprise a sponge, but preferably comprises a synthetic liquid absorbing material such as polyurethane foam, and typically would have a thickness of about one half-inch, the thickness being great enough to provide sufficient liquid-absorbing capacity, but thin enough so that the ultimate pack 10 in which it is utilized can be effectively applied to many body parts. One preferred manner of providing a sufficiency of absorbent material surrounding the piece of foam 15 is by placing multiple wrappings of terry cloth around it as illustrated in FIG. 2. Four sheets of terry cloth are used, two are placed over each major face, 16, 17, surrounding the foam 15, and joined together at seams 18. An envelope of terry cloth 19 is then disposed around layers, 16, 17, (to serve as a casing) and sewn together to form a seam 20; the unit is then sewn with an overall quilting pattern to provide strength and durability. An alternative absorbent material, used in place of 16, 17, would be quilted cotton batting. The ultimate inner core 11 produced (see FIG. 3) is a compact readily handled component which may be readily washed. More importantly, it holds sufficient water to sustain the heat of the pack over long periods of time, and holds the water even when sustaining the pressure of the weight of a human body, or the like. Of course, more layers of terry cloth (e.g., six) can be used if desired.

The inner bag preferably comprises a bag formed of a thermoplastic film, it extends in length approximately one third longer than the inner core it accommodates (see FIG. 3), and its access opening is at one end of its extended length. The excess length is folded over and serves as a flap 23. While a variety of thermoplastic films have sufficient liquid imperviousness for use in the pack 10, such as polyethylene and polypropylene, it is preferred that the inner bag 12 be formed of nylon. While polyethylene and polypropylene are, like nylon, microwave-transparent, after repeated use the high temperatures of the liquid (and steam) within the bag 12 can result in undesirable welding of the flap 23 to the body of the bag 12 if it is of polyethylene or polypropylene. A nylon bag, such as a commercially available nylon cooking bag manufactured by Reynolds Metals Company of Richmond, Va. (designed for use in conventional and microwave ovens), is eminently suited for use in practicing the present invention.

The outer covering 13 preferably comprises an elongated envelope of an insulating fabric-like material that is microwave-transparent. One such material eminently suited for practicing the present invention is conventional self-lined drapery fabric, flocked or unflocked. This material normally comprises a fabric base 26 with a foam lining 27, which lining may be flocked. Typical of such material is that disclosed in U.S. Pat. Nos. 3,527,654 and 4,056,646, the disclosures of which are hereby incorporated by reference herein. The desired properties of the outer envelope are that it have good insulation qualities, good shape retention, and ready washability. The heat retention of the pack is much greater utilizing such an outer covering 13 than if a simple piece of cloth, or the like, were provided.

The outer covering 13 preferably is permanently closed around its periphery except at open end 30 thereof. The open end 30 may be closed by conventional snap-fasteners, or hook and pile-type fasteners (such as those sold under the trademark "Velcro"). Exemplary hook and pile fasteners are shown by reference numeral 31 in FIGS. 2 and 3. The envelope defining the outer covering 13 preferably is substantially longer than the inner core 11 and the inner bag 12, as clearly illustrated in FIGS. 2 through 6, so that it may be folded-over and overlie one major face of the inner core 11. That is, the portion 33 thereof overlapping the core 11 may be folded-over the core (see FIGS. 5 and 6) to provide a multiple thickness of the insulating cover material 26, 27 along one of the major faces of the core 11, while the other major face has only a single-thickness of outer insulating material 26, 27. This facilitates utilization of the pack, extending the time that it can be effectively applied to a body part. Utilizing a pack 10 according to the present invention, it is possible to apply therapeutic heat to a body part for 30–40 minutes, and to provide some measure of heat for over an hour.

In order to facilitate utilization around some body parts (like an elbow, ankle, or the like), cooperating fasteners may be provided on the overlapping portion 33 and adjacent the closed end of the outer covering envelope 13. For instance, strips of conventional hook and pile fasteners 35 may be diposed adjacent the closed end of the outer covering 13 aong the direction of elongation thereof, while cooperating strips of hook and pile fasteners 36 may be disposed adjacent to open end 30 extending along the width of the envelope 13, as most clearly illustrated in FIGS. 1 and 2. This allows the pack 10 to be wrapped around a body part such as an elbow, as illustrated in FIG. 5.

The practice of the method according to the present invention is readily apparent from an inspection of FIGS. 3 through 6. The inner core 11 is substantially saturated with liquid, and then is inserted into the inner bag 12 through access opening 22. The flap 23 is then closed, although there is no requirement that it be fastened shut. The inner bag 12 is then passed into the outer covering 13 through the access opening 30, and the fasteners 31 are moved together to close the access opening 30. This is all illustrated in FIG. 3.

After the heat pack 10 is appropriately assembled, it is placed—as illustrated schematically in FIG. 4—in operative association with a microwave source 40. This would be accomplished most easily, of course, by merely placing the pack 10 inside a microwave oven, an enclosure for such an oven being illustrated schematically be reference numeral 41 in FIG. 4. Microwaves heat the water held by the inner core 11, but do not significantly heat the rest of the components of the pack 10, those components being "microwave-transparent". Heating may be practiced for any desired period of time, but 2–7 minutes is normally sufficient. During this time, a substantial portion of the water may be turned to steam, which is held within the impervious inner bag 12. By conduction, the hot liquid or steam held by, and associated with, the inner core 11 heats inner bag 12 and outer covering 13.

After removal of the pack 10 from operative association with the microwave source 40, the pack 10 is placed in association with a body part. For instance as illustrated in FIG. 5, the pack 10 is wrapped around a person's elbow. It is held in place at the position desired by the hook and pile fasteners 35, 36 engaging each other.

Another manner in which the pack 10 may be utilized is illustrated in FIG. 6. In FIG. 6, the overlapping flaps 33 have been folded-over one of the major faces of the core 11, providing three thicknesses of the insulating outer covering material 26, 27 at one face of the pack 10, and only one thickness at the other face. As illustrated in FIG. 6, the three-thickness face may then be placed directly on the body parts to be heated. This may be done directly after removal from the microwave oven 41 since the insulating properties provided by the overlapping section are sufficient to prevent burning of the skin, or the like. After the temperature of the pack 10 equalizes somewhat with the ambient temperature, the pack can be flipped over (as indicated by the arrow in FIG. 6) so that the single-thickness face thereof is brought into contact with a human body part. By that time, the single-thickness face of the pack 10 will be sufficiently cool so that it will not injure the user's skin, and there will be a greater heat-transfer therethrough than through the other triple-thickness face. In this way, therapeutic heat can be applied to a body part for 30-45 minutes.

When it is desired to re-use the pack 10 according to the present invention to apply therapeutic heat, it is not necessary to disassemble the components of the pack, or the like. Rather it is only necessary to place the pack 10 back in the microwave oven 41, heat it for the predetermined desired time, and again remove it and apply it to the desired body parts. The pack 10 can be re-used many times before it is necessary to remove the inner core 11 and again substantially saturate it with liquid.

While the pack 10 has been illustrated having particular relative dimensions in the drawings, the dimensions of the pack 10 are not limited by the exemplary embodiment in the drawings, but rather the pack 10 may assume a wide variety of shapes and forms, and have a wide variety of dimensions.

The heat-transfer pack 10 according to the present invention may be held in association with body parts to be treated in any desired manner. For instance, it may be merely laid on the body part, the weight of the entire body part may be applied onto the pack, or an elastic bandage or accessory straps or straps integral with the pack 10 may be utilized to hold it in place. The pack 10 can be used for applying cold by putting cold liquid, or crushed ice, in association with inner core 11.

It will thus be seen that according to the present invention a simple, readily utilizable, inexpensive, and effective therapeutic heat-transfer pack, and a simple and effective method of applying moist therapeutic heat to a body part, have been provided.

While the invention has herein been described in what is presently conceived to be a practical and preferred embodiment thereof, it will be apparent to those of ordinary skill in the art that many modifications may be made thereof within the scope of the invention, which scope should be accorded the broadest interpretation of the appended claims so as to encompass all equivalent structures and methods.

What is claimed is:

1. A method of applying therapeutic heat to a mammal body part utilizing a heat pack including a liquid-absorbing inner core, a liquid-impervious microwave-transparent inner bag, and an outer microwave-transparent covering, comprising the steps of substantially sequentially:
    (a) applying liquid to the core so that it is substantially saturated;
    (b) disposing the core in the inner bag, and closing the bag;
    (c) disposing the closed inner bag and core in the outer covering;
    (d) disposing the heat pack in operative association with a microwave source to heat the liquid associated with the core; and
    (e) removing the heat pack from association with the microwave source and placing it in contact with a body part to be treated.

2. A method as recited in claim 1 comprising the further step of, after cooling of the heat pack, merely re-disposing the heat pack in association with the microwave source to reheat the liquid, without repeating steps (a)-(c), and repeating step (e).

3. A method as recited in claim 1 or 2 wherein the outer covering of the pack has a pair of major faces, and greater heat insulation at one major face thereof than at the opposite major face thereof; and wherein step (e) is practiced by placing the major face of the pack with greater heat insulation in direct contact with the body part to be heated directly after removal of the heat pack from association with the microwave source, and, after some cooling of the heat pack, placing the major face of the heat pack with less insulation in contact with the body part to be treated.

4. A method as recited in claims 1 or 2 wherein the heat pack outer covering includes cooperating fasteners formed on opposite faces thereof, and wherein step (e) is practiced by wrapping the heat pack around the body part to be treated so that the fasteners are brought into operative association with each other and hold the heat pack in place.

5. A method as recited in claims 1 or 2 wherein step (b) is practiced by disposing the core in a nylon film inner bag.

6. A method as recited in claims 1 or 2 wherein step (c) further includes temporarily and releasably closing the outer covering.

7. A method as recited in claims 1 or 2 wherein the outer covering has first and second opposite faces, and a much greater length than that of the inner core, in use, so that the outer covering has a portion overlapping the core after practice of step (c); and wherein step (e) is practiced by:
    (f) folding the overlapping portion onto the first face of the outer covering to form a multiple-layer face;
    (g) placing the multiple-layer first face into contact with the body part; and then
    (h) after the passage of a period of time during which the pack cools, removing the pack first face from the body part, and placing the second face, which is not a multiple-layer, into contact with the body part;
    whereby during an early stage of treatment with the pack the face with minimum heat is in contact with the body part, and during a later stage of treatment the face with the maximum heat is in contact with the body part.

8. A method as recited in claim 7 wherein step (b) is practiced by disposing the core in a nylon film inner bag.

* * * * *